United States Patent [19]

Yoshida

[11] Patent Number: 5,008,624
[45] Date of Patent: Apr. 16, 1991

[54] NUCLEAR MAGNETIC RESONANCE IMAGING APPARATUS FOR ARBITRARY PATIENT POSTURE

[75] Inventor: Tadatoki Yoshida, Tochigi, Japan

[73] Assignee: Kabushiki Kaisha Toshiba, Kawasaki, Japan

[21] Appl. No.: 373,583

[22] Filed: Jun. 30, 1989

[30] Foreign Application Priority Data

Jul. 6, 1988 [JP] Japan .................................. 63-166856

[51] Int. Cl.⁵ .............................................. G01R 33/20
[52] U.S. Cl. .................................................... 324/318
[58] Field of Search ................ 378/209; 324/300, 307, 324/309, 318, 319, 320, 322; 128/653

[56] References Cited

U.S. PATENT DOCUMENTS

| 2,947,920 | 8/1960 | Hall | 324/319 |
|---|---|---|---|
| 3,506,826 | 4/1970 | Kosters | 378/209 |
| 3,724,004 | 4/1973 | Behrens | 378/209 |
| 4,354,499 | 10/1982 | Damadian | 324/309 |
| 4,534,358 | 8/1985 | Young | 324/318 |
| 4,727,328 | 2/1988 | Carper et al. | 324/318 |
| 4,771,785 | 9/1988 | Duer | 324/318 |

Primary Examiner—Michael J. Tokar
Attorney, Agent, or Firm—Foley & Lardner

[57] ABSTRACT

A nuclear magnetic resonance imaging apparatus which does not cause any unnecessary mental disturbances in the object, and which is capable of taking images with patient's postures other than lying flat. The apparatus includes a main magnet having two separated poles arranged in parallel for generating a static magnetic field in an open space between the two poles; and a carrier for carrying an object to be examined into the static magnetic field, capable of supporting the object at arbitrary angles with respect to a floor.

18 Claims, 6 Drawing Sheets

NUCLEAR MAGNETIC RESONANCE IMAGING APPARATUS FOR ARBITRARY PATIENT POSTURE

BACKGROUND OF THE INVENTION

1. Field of the Invention

The present invention relates to an nuclear magnetic resonance imaging apparatus for taking arbitrary tomographic images of an object to be examined by utilizing a nuclear magnetic resonance phenomena.

2. Description of the Background Art

As is well known, a nuclear magnetic resonance imaging apparatus obtains arbitrary tomographic images of an object to be examined by detecting nuclear magnetic resonance signals induced by applying high-frequency excitation magnetic field (referred hereafter as RF-pulse) on the object placed in a static magnetic field, under a presence of gradient magnetic fields, and then analyzing the detected nuclear magnetic resonance signals to derive information on distributions of densities of particular nuclei and longitudinal and transverse relaxation times, from which arbitrary tomographic images are constructed by methods of image reconstruction processing.

Figure 1:
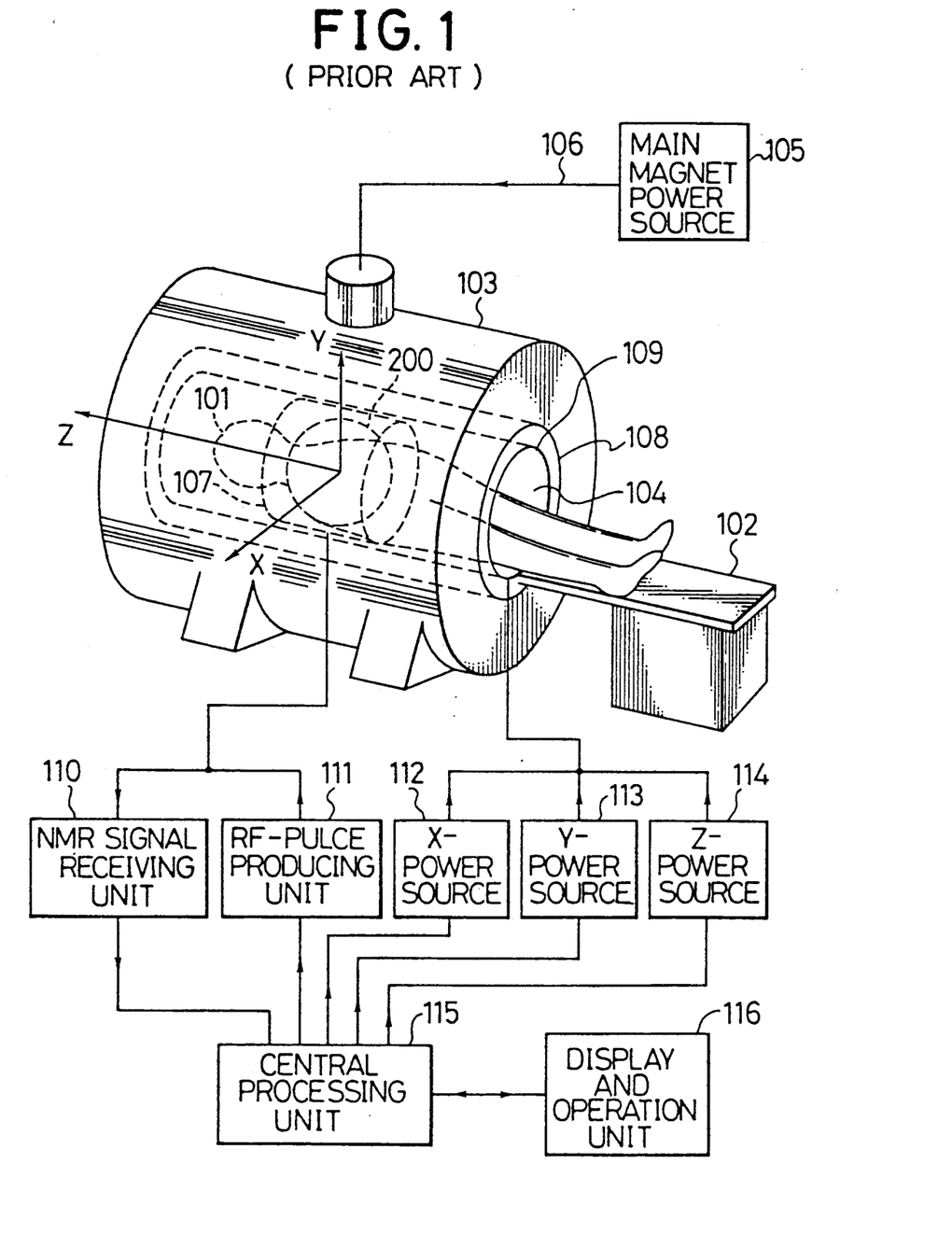
FIG. 1 is a diagram of a typical conventional nuclear magnetic resonance imaging apparatus.

A typical conventional nuclear magnetic resonance imaging apparatus is shown in FIG. 1. In this nuclear magnetic resonance imaging apparatus, a patient 101 is placed on a bed 102 extending into a bore 104 of a main magnet 103 in which a static magnetic field is generated by the main magnet 103. This main magnet 103 can be any one of a superconductive magnet, a normal temperature electromagnet, and a permanent magnet. Except when the main magnet 103 is a permanent magnet, this main magnet is magnetized and de-magnetized by a main magnet power source 105 through a lead cable 106. When the main magnet 103 is a superconductive magnet, this lead cable 106 will be removed after the magnetization in order to minimize consumption of liquid helium coolant, which is possible because the superconductive magnet can operate in a permanent current mode once magnetized.

The bore 104 is further inside equipped with a transceiver coil 107 for producing Rf-pulses and receiving nuclear magnetic resonance signals, a shim coil 108 for fine-adjustment for magnetic fields inside the bore 104, and a gradient coil 109 for producing gradient magnetic fields. The transceiver coil 107 comprises a transmitter coil and a receiver coil which are connected to a nuclear magnetic resonance signal receiving unit 110 and an RF-pulse producing unit 111, respectively. The gradient coil 109 comprises an X-coil, Y-coil, and Z-coil which are connected to X-power source 112, y-power source 113, and z-power source 114, respectively. All of the nuclear magnetic resonance signal receiving unit 110, RF-pulse producing unit 111, X-power source 112, Y-power source 113, and Z-power source 114 are controlled by a central processing unit 115 which also carries out all the analysis of the detected nuclear magnetic resonance signals. This central processing unit 115 is also connected to a display and operation unit 116 at which the obtained tomographic images are displayed and from which it is operated.

In such a nuclear magnetic resonance imaging apparatus, a imaging takes place in an uniform magnetic field region 200. In order to obtain a tomographic image for a complete slice of the patient 101, it is necessary for this uniform magnetic field region 200 to be a sphere wtih a diameter of 40 to 50 cm and less than 50 ppm field fluctuation. To meet such requirements, the main magnet 103 becomes as large as 2.4 m in length, 2 m in width, 2.4 m in height, and 5 to 6 tons in weight, when the main magnet 103 is a superconductive magnet. Moreover, since the main magnet 103 alone can produce a sphere of 40 to 50 cm diameter with only about few hundreds ppm field fluctuation at best, the additional use of the shim coil 108 is indispensable in achieving the required less than 50 ppm field fluctuation.

As briefly mentioned above, the imaging is carried out by detecting with the transceiver coil 107. The nuclear magnetic resonance signals are induced from a portion of the patient 101 placed within the uniform magnetic field region 200 by applying RF-pulses from the transceiver coil 107 along with the gradient magnetic fields from the gradient coil 109, which is under the control by the central processing unit 115. The central processing unit 115 then analyze the detected nuclear magnetic resonance signals to derive information on distributions of densities of particular nuclei and longitudinal and transverse relaxation times, from which arbitrary tomographic images to be displayed at the display and operation unit 116 are contructed by methods of image reconstruction processing.

Such a conventional nuclear magnetic resonance imaging apparatus presents the following problems.

First, it is necessary, because of the configuration described above, to insert the patient 101 into a narrow bore 104, which in a practical medical circumstances causes an unnecessary mental disturbances in the patient 101.

Secondly, it is necessary, again because of the configuration described above, to lay the patient 101 flat on the bed 102. However, in a case of a patient suffering from spinal hernia caused by excessive pressure on spine and spinal chord in a standing posture for instance, it is actually preferred to have an image taken in a standing posture. However, imaging in such a posture other than lying flat is not possible in the conventional nuclear magnetic resonance imaging apparatus described above.

SUMMARY OF THE INVENTION

It is therefore an object of the present invention to provide a nuclear magnetic resonance imaging apparatus which does not cause any unnecessary mental disturbances in the patient, and which is capable of taking images with patient's postures other than lying flat.

According to one aspect of the present invention there is provided a nuclear magnetic resonance imaging apparatus, comprising: a main magnet having two separated poles arranged in parallel for generating a static magnetic field in an open space between the two poles; and carrier means for carrying a patient to be examined into the static magnetic field, capable of supporting the patient at arbitrary angles with respect to a floor.

Other features and advantages of the present invention will become apparent from the following description taken in conjunction with the accompanying drawings.

DETAILED DESCRIPTION OF THE PREFERRED EMBODIMENTS

Figure 2A:
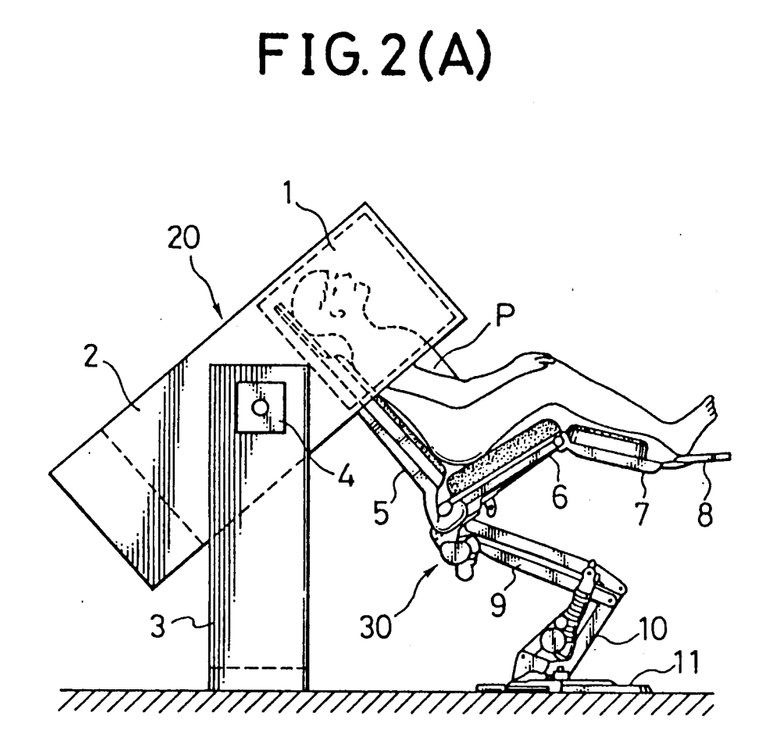
FIGS. 2(A) and (B) are side and front views, respectively, of one embodiment of a nuclear magnetic resonance imaging apparatus according to the present invention.
Figure 2B:
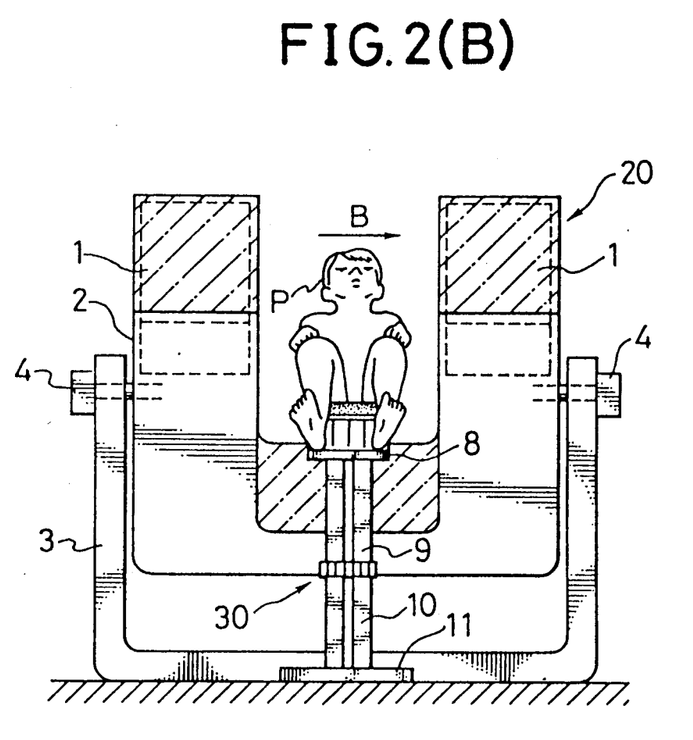

Referring now to FIGS. 2(A) and 2(B), there is shown one embodiment of a nuclear magnetic resonance imaging apparatus according to the present invention.

In this embodiment, a main magnet 20 is comprised of a pair of superconductor blocks 1 facing each other placed at two ends of a metallic U-shaped frame 2, a supporting member 3 fixed to a floor which supports the U-shaped frame 2 at approximate middle points of its two legs in rotatable manner, and a driver 4 for driving the U-shaped frame 2 in rotation. Details of the superconductor blocks 1 will be described below.

This embodiment further includes a patient carrier 30 in a form of a chair equipped with a lifting mechanism and a reclining mechanism, comprised of an upper body rest 5, a seat 6, a leg rest 7, and a foot rest 8 all of which are connected and adjustable at arbitrary angles by means of locking mechanisms provided in between, an upper arm 9 and a lower arm 10 connected by a linking mechanism for providing the lifting mechanism, and a base 11 for mounting a whole patient carrier 30 on the floor.

The main magnet 20 and the patient carrier 30 are arranged in such a way a back of the upper body rest 5 can face towards a bottom beam of the U-shaped frame 2, as can be seen from FIGS. 2(A) and 2(B) which depict a situation in which an upper body of a patient P is ready for image taking as being placed in a static magnetic field B generated between the superconductor blocks 1. Thus, by suitably rotating the U-shaped frame 2 of the main magnet 20 or by lifting up and down the patient carrier 30 with the lifting mechanism, variously different various relative orientations of the main magnet 20 and the patient carrier 30 are realizable, so that not only different parts of the patient P can be placed in a region of a sufficiently uniform magnetic field but also with a help of the reclining mechanism the imaging can be performed with the patient P taking various postures.

Figure 3:
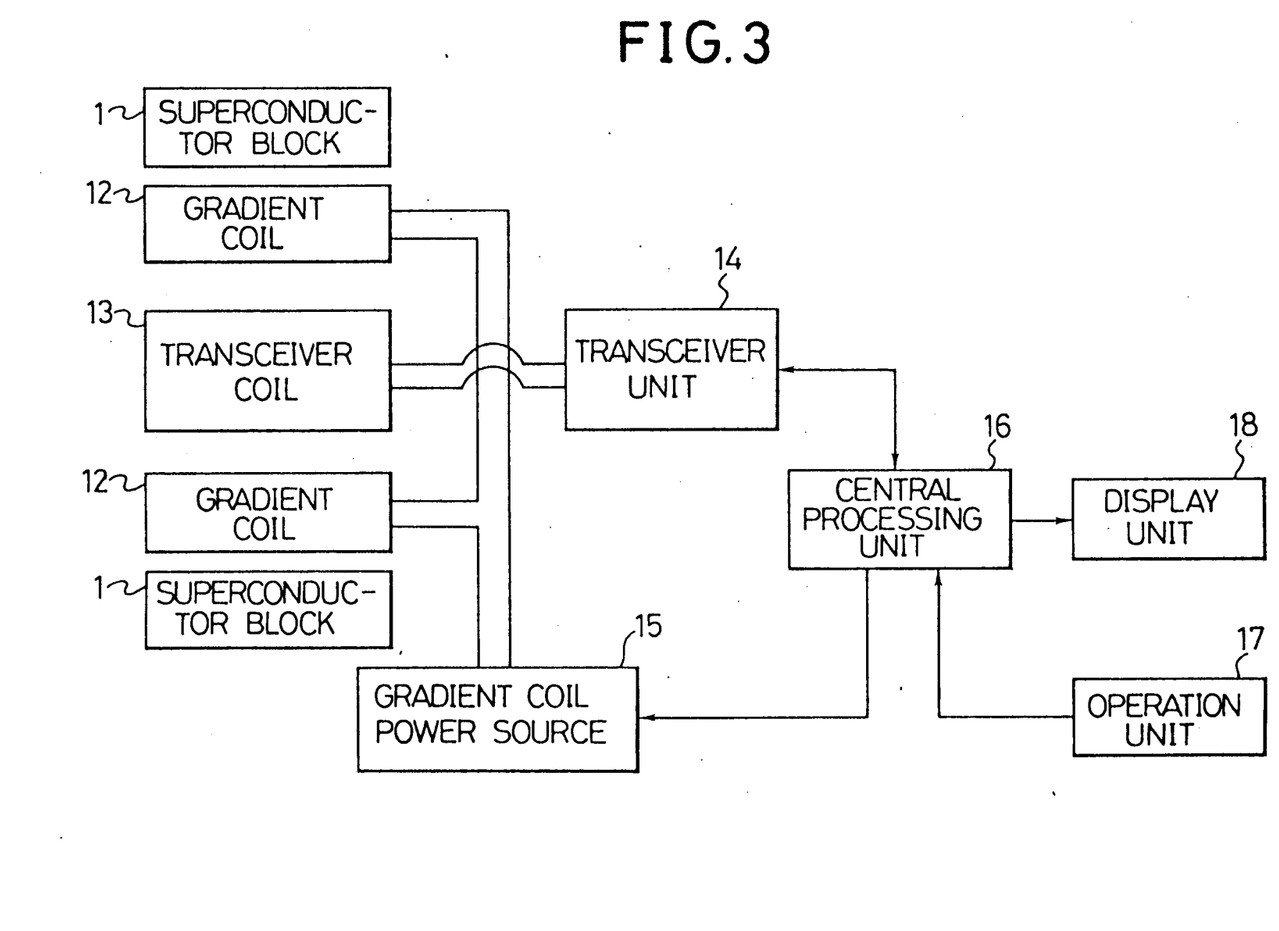
FIG. 3 is a block diagram for the embodiment of a nuclear magnetic resonance imaging apparatus shown in FIGS. 2(A) and (B).

Other features of this embodiment are shown in FIG. 3, where there are a gradient coil 12 for producing the gradient magnetic field in X-, Y-, and Z-directions and a transceiver coil 13 for producing RF-pulses and receiving nuclear magnetic resonance signals, both of which are to be placed in the static magnetic field B between the superconductor blocks 1. The transceiver coil 13 is connected to a transceiver unit 14 for controlling the transceiver coil 13 in two functions of transmitter of the RF-pulses and the receiver of the nuclear magnetic resonance signals, while the gradient coil 12 is connected to a power source 15. The transceiver unit 14 and the power source 15 are controlled by a central processing unit 16 which also carries out all the analysis of the detected nuclear magnetic resonance signals. The central processing unit 16 is operated from an operation unit 17. The resulting tomographic images are displayed at a display unit 18. All these features of this embodiment other than the main magnet 20 and the patient carrier 30 can, when taken singly, substantially be the same as corresponding parts of a conventional nuclear magnetic resonance apparatus.

Now, details of the superconductor blocks 1 will be described.

First of all, each of the superconductor blocks 1 is manufactured as follows.

Figure 4:
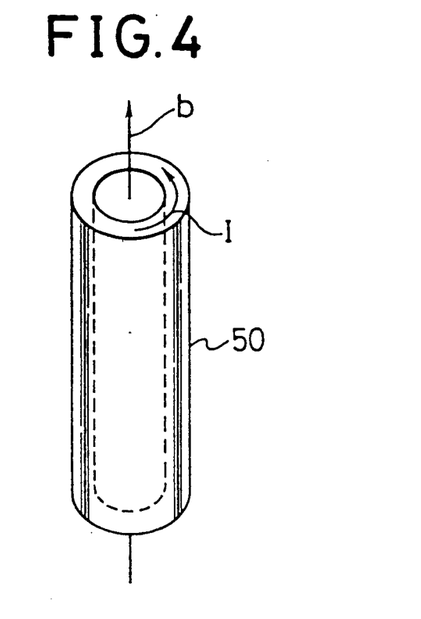
FIG. 4 is an illustration of a superconductor cylinder which may be utilized in the embodiment of a nuclear magnetic resonance imaging apparatus shown in FIGS. 2(A) and (B).
Figure 5:
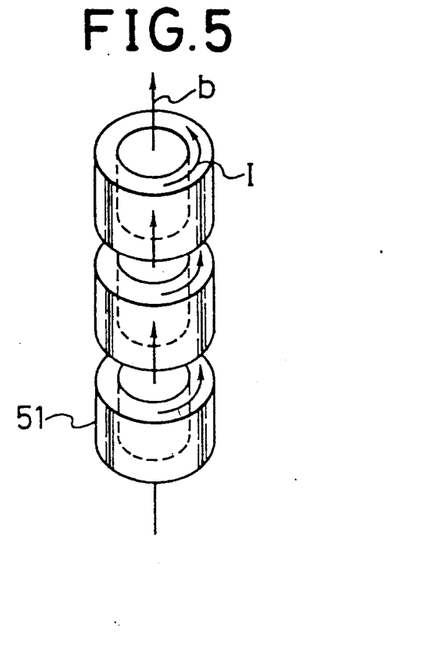
FIG. 5 is an illustration of superconductor rings which may be utilized in the embodiment of a nuclear magnetic resonance imaging apparatus shown in FIGS. 2(A) and (B).

A ceramic superconductive material such as Y-Ba-Cu-O type ceramic which becomes a superconducting state above a liquid Nitrogen temperature (77° K.) is sintered into a superconductive body in a form of either a superconductive cylinder 50 as shown in FIG. 4, or superconductive rings 51 as shown in FIG. 5. Because when only ceramics are sintered there appears rather large air gaps between particles of the ceramics, it is preferable to carry out the sintering with ceramics mixed with metal powders of high electrical conductivity such as that of Pb(lead), In(indium), Cu(copper), and Al(aluminum), so that such metal powders can fill in the air gaps and superconductive body 50/51 with better electrical characteristics can be obtained.

Figure 6A:
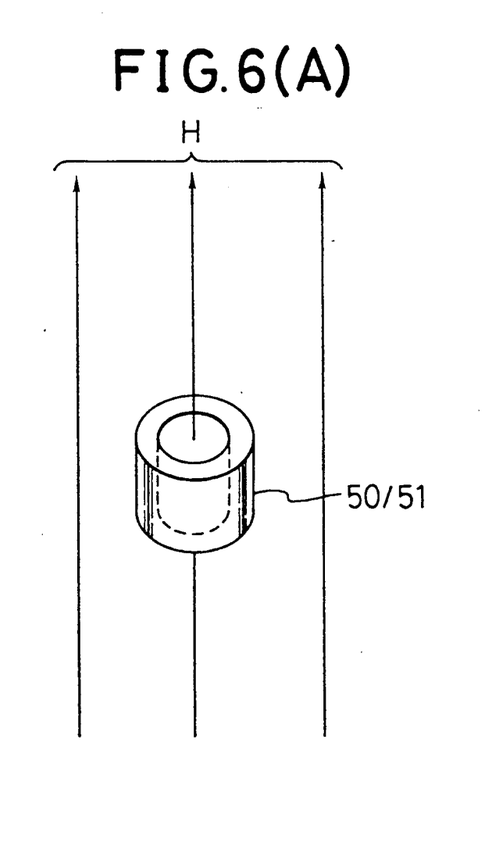
FIGS. 6(A) and 6(B) are illustrations of one superconductor ring of FIG. 5 for explaining its properties with and without an external magnetic field, respectively.
Figure 6B:
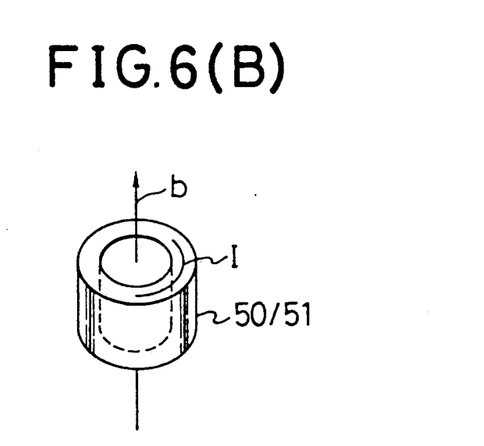

Superconductive bodies 50/51 thus manufactured are then placed in an external magnetic field H while being maintained to be in a superconductive state (i.e. at a temperature below the critical temperature), as shown in FIG. 6(A) for one superconductive ring 51. When the external magnetic field H is removed later on, a current I which can produce a magnetic field b that is equivalent to the external magnetic field H will be induced in a direction of circumference inside body edges, as shown in FIG. 6(B), which will become a permanent current (i.e., not dissipating) when the superconductive body 50/51 is in a superconductive state so that a constant magnetic field b along the axis of the superconductive body 50/51 will persist.

In a case of the superconductive ring 51, a plurality of such superconductive rings 51 are compiled coaxially, as in FIG. 5, and this structure can contribute to improved uniformity and accuracy in strength as well as homogeneity of the magnetic field b.

Figure 7:
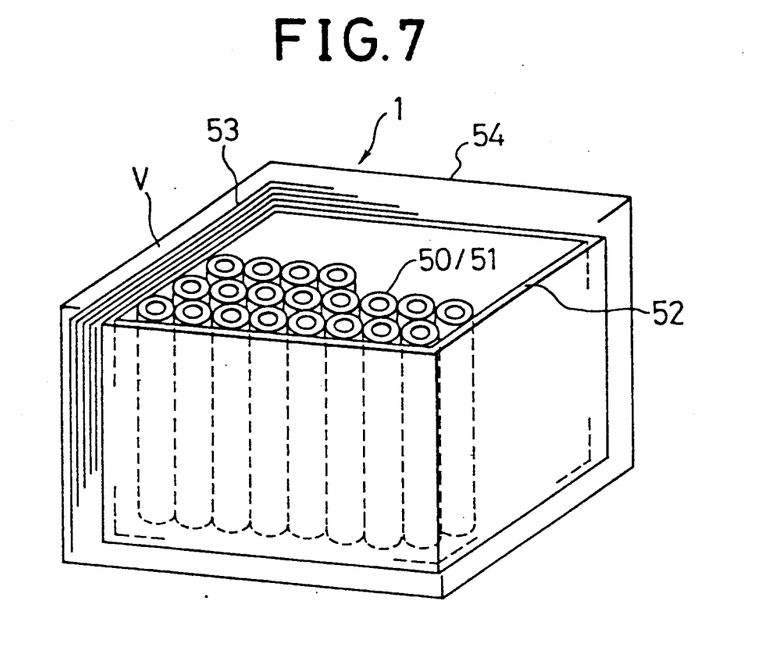
FIG. 7 is a perspective view of a superconductor block to be utilized in the embodiment of a nuclear magnetic resonance imaging apparatus shown in FIGS. 2(A) and 2(B).

Such superconductive bodies 50/51 with a constant magnetic field b along the axis are then installed in a liquid Nitrogen container 52 filled with liquid Nitrogen, with the direction of the magnetic field b aligned in one direction, as shown in FIG. 7. This liquid Nitrogen container 52 is surrounded by a heat insulator 53 and installed in a vacuum container 54 to have a vacuum layer V further surrounding it.

A cryostat structure thus composed will be used as each of the superconductor blocks 1. It is to be noted that the liquid Nitrogen container 52 can be directly cooled by means of a small freezer such as a Gifford-MachMahon system. Also, the magnetization of the superconductive body 50/51 by the external magnetic field H can be carried out after the superconductive block 1 of the cryostat structure has been constructed.

Figure 8:
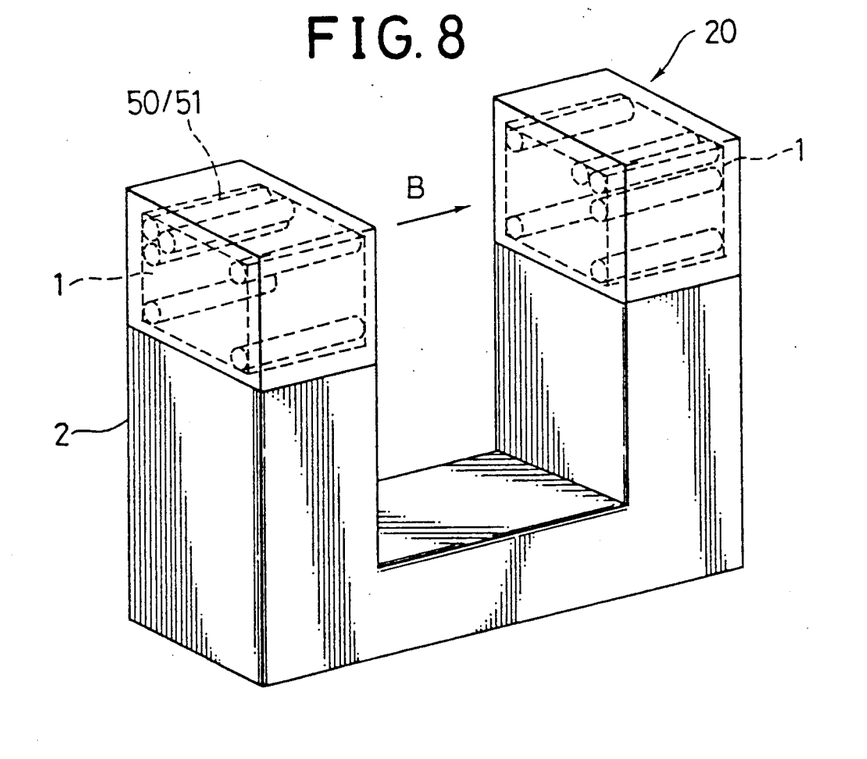
FIG. 8 is a perspective view of a main magnet of the embodiment of a nuclear magnetic resonance imaging apparatus shown in FIGS. 2(A) and 2(B).

Two of the Superconductor blocks 1 thus constructed are then installed at each end of the U-shaped frame 2 in parallel, as shown in FIG. 8, such that the static magnetic field B can be generated between the ends of the U-shaped frame 2.

Figure 9:
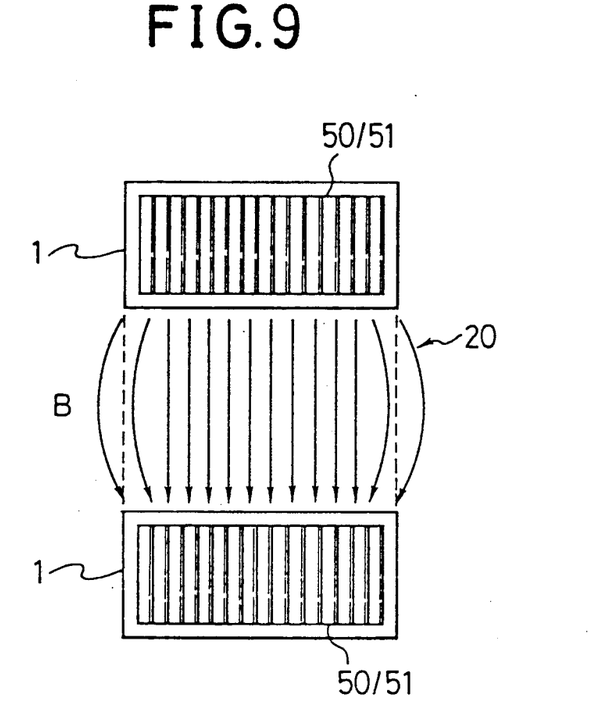
FIG. 9 is a diagrammatic illustration of one possible situation for the main magnet shown in FIG. 8 and the static magnetic field generated by this main magnet.
Figure 10:
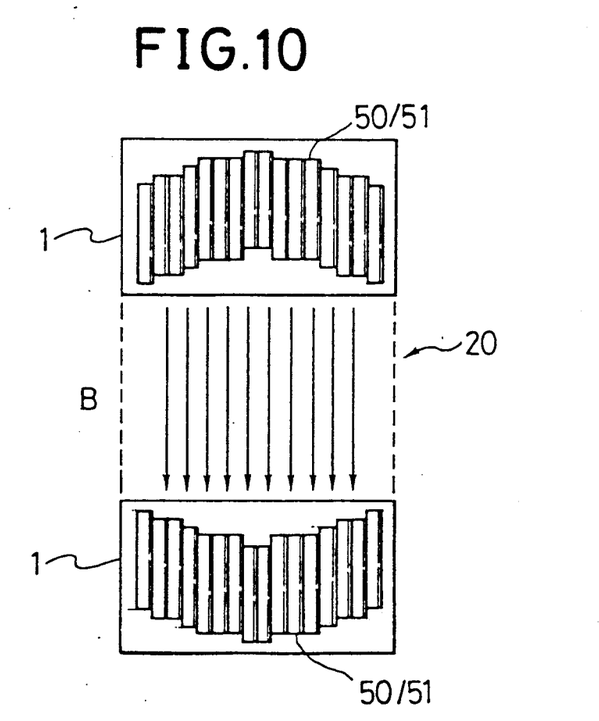
FIG. 10 is a diagrammatic illustration of another possible situation for the main magnet shown in FIG. 8 and the static magnetic field generated by this main magnet.

Now, the uniformity of the static magnetic field B can be improved by making a cross sectional area of each superconductive body 50/51 sufficiently smaller compared with that of the superconductive block 1. However, when two superconductor blocks 1 are arranged in parallel, facing each other, as in the case for the construction of the main magnet 20 just described, an extent of uniformity achievable is limited by an appearance of the edge effects, as shown in FIG. 9. Namely, the magnetic field near the edge portion of the superconductor block 1 tends to deviate. For this reason, it is preferable to equip each superconductor block 1 with a mechanism for finely adjusting positions along the axis of individual superconductive body 50/51, such that the deviation due to the edge effect can be corrected, as shown in FIG. 10, by bringing those superconductive bodies 50/51 near the edges of each of the superconductor blocks 1 closer to each other than other superconductive bodies 50/51.

This main magnet 20 composed by two superconductor blocks 1 is highly advantageous in that it can produce the static magnetic field sufficiently strong for the purposes of high-speed imaging and spectroscopic application of the nuclear magnetic resonance imaging apparatus, its maintenance can be quite simple and inexpensive since liquid Nitrogen is used, it can be manufactured inexpensively as the superconductive body 50/51 can be manufactured inexpensively. In addition it is lighter in weight since ceramics are used, and an amount of leakage of magnetic field to an external region can be reduced by means of the metallic U-shaped frame 2. No shim coil is necessary as fine-adjustment of the static magnetic field can be achieved by means of the mechanism for finely adjusting positions along the axis of individual superconductive body 50/51, and its running cost can be reduced because of the cryostat structure of the superconductor blocks 1 and because of the use of the permanent currents as a source of the static magnetic field it produces.

Although these advantages are specific for the main magnet 20 with superconductor blocks 1, the main magnet 20 of permanent magnet type or of electromagnet type may be employed with benefits coming from novel configuration of the main magnet 20 and the patient carrier 30 shown in FIGS. 2(A) and 2(B).

Thus, according to this embodiment, it is possible to provide a nuclear magnetic resonance imaging apparatus which does not cause any unnecessary mental disturbances in the patient, since the imaging takes place in the static magnetic field generated in open air between end of the U-shaped main magnet 20 which makes it unnecessary to insert the patient into a narrow space such as that inside the bore of the main magnet in a conventional nuclear magnetic resonance imaging apparatus.

Moreover, according to this embodiment, it is further possible to provide a nuclear magnetic resonance imaging apparatus which is capable of taking images with patient's postures other than lying flat, because of the configuration of the main magnet 20 and the patient carrier 30 which is readily adaptable to any desired posture of the patient including a standing posture as well as a lying flat posture.

In addition, by using the superconductor blocks 1 for the main magnet 20, various advantages enumerated above can simultaneously be obtained.

It is to be noted that many modifications and variations of the above embodiment may be made without departing from the novel and advantageous features of the present invention. Accordingly, all such modifications and variations are intended to be included within the scope of the appended claims.

What is claimed is:

1. A nuclear magnetic resonance imaging apparatus, comprising;
    a main magnet having two physically disconnected poles arranged in parallel for generating a static magnetic field in an open space between the two physically disconnected poles each of the two physically disconnected poles being made of a superconductor block capable of producing a magnetic field independently; and
    carrier means for carrying an object to be examined into the static magnetic field, capable of supporting the object at arbitrary angles with respect to a floor.

2. The apparatus of claim 1, wherein the two physically disconnected poles are placed at two ends of a U-shaped frame.

3. The apparatus of claim 1, wherein the main magnet comprises:
    holding means for holding the two physically disconnected poles in parallel;
    means for supporting the holding means in a rotatable manner; and
    means for driving the holding means in a rotational motion.

4. The apparatus of claim 1, wherein the carrier means comprises an upper body rest and an lower body rest, at least one of the upper body rest and the lower body rest being reclinable.

5. The apparatus of claim 4, wherein the carrier means is in a form of a chair equipped with a reclining mechanism.

6. The apparatus of claim 1, wherein the carrier means further includes means for lifting the object up and down with respect to the floor.

7. The apparatus of claim 1, wherein the superconductor block is comprised of a plurality of superconductive bodies each of which having a permanent current circulating within itself.

8. The apparatus of claim 7, wherein the superconductor block has a cryostat structure comprising;
    a coolant container filled with coolant, into which the superconductive bodies are installed;
    a heat insulator surrounding the coolant container; and
    a vacuum container with a vacuum layer surrounding the heat insulator.

9. The apparatus of claim 7, wherein the superconductor block comprises:
a coolant container filled with coolant, into which the superconductive bodies are installed; and
freezer means for cooling the coolant container.

10. The apparatus of claim 7, wherein each of the superconductive body comprises a plurality of superconductive rings compiled coaxially.

11. The apparatus of claim 10, wherein each of the superconductive rings is made of sintered ceramic superconductive materials which are in superconducting state above a temperature of liquid Nitrogen.

12. The apparatus of claim 11, wherein the superconductive rings are manufactured by sintering the ceramic superconductive materials with metal powder of high electrical conductivity mixed.

13. The apparatus of claim 7, wherein each of the superconductive body comprises a plurality of superconductive cylinders.

14. The apparatus of claim 13, wherein each of the superconductive cylinders is made of sintered ceramic superconductive materials which are in superconducting state above a temperature of liquid Nitrogen.

15. The apparatus of claim 14, wherein the superconductive cylinders are manufactured by sintering the ceramic superconductive materials with metal powder of high electical conductivity mixed.

16. The appartus of claim 7, wherein the superconductive block is constructed by assembling the plurality of superconductive bodies each of which having a permanent current circulating within itself before being assembled.

17. The appartus of claim 7, wherein the superconductive block is constructed by assembling the plurality of superconductive bodies within each of which a permanent current is induced to circulate after being assembled.

18. The apparatus of claim 7, wherein the superconductor block further include means for finely adjusting positions of each superconductive body in a direction of the static magnetic field.

* * * * *